United States Patent

(12) United States Patent
Hannesson et al.

(10) Patent No.: US 11,185,430 B2
(45) Date of Patent: Nov. 30, 2021

(54) PROSTHETIC ATTACHMENT SYSTEM AND CORRESPONDING LOCK ASSEMBLY

(71) Applicant: Ossur Iceland ehf, Reykjavik (IS)

(72) Inventors: Sigurdur Hannesson, Reykjavik (IS); Andrew Bache, Reykjavik (IS); Dadi Granz, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 51 days.

(21) Appl. No.: 16/739,570

(22) Filed: Jan. 10, 2020

(65) Prior Publication Data
US 2020/0222211 A1 Jul. 16, 2020

Related U.S. Application Data

(60) Provisional application No. 62/790,679, filed on Jan. 10, 2019.

(51) Int. Cl.
A61F 2/78 (2006.01)
A61F 2/80 (2006.01)

(52) U.S. Cl.
CPC .............. A61F 2/78 (2013.01); A61F 2/80 (2013.01); A61F 2002/7875 (2013.01)

(58) Field of Classification Search
CPC ....... A61F 2002/7875; A61F 2/78; A61F 2/80
See application file for complete search history.

(56) References Cited

U.S. PATENT DOCUMENTS

| 980,457 | A | 1/1911 | Toles |
|---|---|---|---|
| 1,398,824 | A | 11/1921 | Abrams |
| 1,893,853 | A | 1/1933 | Tullis |
| 2,530,285 | A | 11/1950 | Catranis |
| 2,533,404 | A | 12/1950 | Sharp et al. |
| 2,634,424 | A | 4/1953 | Gorman |
| 2,671,225 | A | 3/1954 | Schoene et al. |

(Continued)

FOREIGN PATENT DOCUMENTS

| CN | 1793681 A | 6/2006 |
|---|---|---|
| DE | 745981 C | 5/1944 |

(Continued)

OTHER PUBLICATIONS

English Translation of Chinese Office Action, Chinese Patent Application No. 201480010447.5, dated Mar. 3, 2016.

(Continued)

Primary Examiner — Bruce E Snow
(74) Attorney, Agent, or Firm — Workman Nydegger

(57) ABSTRACT

A prosthetic attachment system and corresponding lock assembly for connecting a distal end of a prosthetic liner to a distal end of a prosthetic socket. The lock assembly includes a base arranged to be supported by the distal end of the prosthetic socket, and defining a bore. An attachment pin is arranged to be carried by the prosthetic liner and insertable through the bore. A lock mechanism is arranged to be carried by the base and is rotatable about a rotation axis. The lock mechanism includes a control knob extending outwardly from a side of the base. The attachment pin is arranged to interact with the lock mechanism cause the control knob to spin at least one projection of the control knob about the rotation axis.

15 Claims, 3 Drawing Sheets

(56) References Cited

U.S. PATENT DOCUMENTS

| | | | |
|---|---|---|---|
| 2,808,593 A | 10/1957 | Andersen | |
| 3,393,407 A | 7/1968 | Kandel | |
| 3,671,980 A | 6/1972 | Baird | |
| 4,216,550 A | 8/1980 | Thompson | |
| 4,564,365 A | 1/1986 | Winer et al. | |
| 4,923,474 A | 5/1990 | Klasson et al. | |
| 4,938,775 A | 7/1990 | Morgan | |
| 5,007,937 A | 4/1991 | Fishman et al. | |
| 5,139,523 A | 8/1992 | Paton et al. | |
| 5,163,965 A | 11/1992 | Rasmusson et al. | |
| 5,226,918 A | 7/1993 | Silagy et al. | |
| 5,314,496 A | 5/1994 | Harris et al. | |
| 5,376,129 A | 12/1994 | Faulkner et al. | |
| 5,376,131 A | 12/1994 | Lenze et al. | |
| 5,413,392 A | 5/1995 | Schlack et al. | |
| 5,507,837 A | 4/1996 | Laghi | |
| 5,549,709 A | 8/1996 | Caspers | |
| 5,593,454 A | 1/1997 | Helmy | |
| 5,658,353 A | 8/1997 | Layton | |
| 5,662,715 A | 9/1997 | Slemker | |
| 5,702,489 A | 9/1997 | Slemker | |
| 5,718,925 A | 2/1998 | Kristinsson et al. | |
| 5,728,170 A | 3/1998 | Becker et al. | |
| 5,735,906 A | 4/1998 | Caspers | |
| 5,779,385 A | 7/1998 | Fechter | |
| 5,882,053 A | 3/1999 | Bekins et al. | |
| 5,888,216 A | 3/1999 | Haberman | |
| 5,888,234 A | 3/1999 | Littig | |
| 5,904,722 A | 5/1999 | Caspers | |
| 5,931,872 A | 8/1999 | Lohmann | |
| 5,972,036 A | 10/1999 | Kristinsson et al. | |
| 6,063,125 A | 5/2000 | Arbogast et al. | |
| 6,106,559 A | 6/2000 | Meyer | |
| 6,123,340 A | 9/2000 | Sprafka et al. | |
| 6,136,039 A | 10/2000 | Kristinsson et al. | |
| 6,149,691 A | 11/2000 | Fay et al. | |
| 6,152,645 A | 11/2000 | Sanford | |
| 6,231,616 B1 | 5/2001 | Helmy | |
| 6,231,617 B1 | 5/2001 | Fay | |
| 6,267,787 B1 | 7/2001 | Capper et al. | |
| 6,273,918 B1 | 8/2001 | Yuhasz et al. | |
| 6,287,345 B1 | 9/2001 | Slemker et al. | |
| 6,334,876 B1 | 1/2002 | Perkins | |
| 6,361,568 B1 | 3/2002 | Hoerner | |
| 6,402,789 B1 | 6/2002 | Gramnas | |
| 6,440,173 B1 * | 8/2002 | Meyer | A61F 2/76 623/36 |
| 6,485,776 B2 | 11/2002 | Janusson et al. | |
| 6,508,842 B1 | 1/2003 | Caspers | |
| 6,554,868 B1 | 4/2003 | Caspers | |
| 6,585,774 B2 | 7/2003 | Dean, Jr. et al. | |
| 6,596,027 B2 | 7/2003 | Laghi | |
| 6,596,028 B1 | 7/2003 | Laghi | |
| 6,605,118 B2 | 8/2003 | Capper et al. | |
| 6,626,951 B1 | 9/2003 | Gramnas | |
| 6,645,253 B2 | 11/2003 | Caspers | |
| 6,726,726 B2 | 4/2004 | Caspers | |
| 6,761,742 B2 | 7/2004 | Caspers | |
| 7,056,303 B2 | 6/2006 | Dennis et al. | |
| 7,217,060 B2 * | 5/2007 | Ingimarsson | A61F 2/60 403/105 |
| 7,234,108 B1 | 6/2007 | Carstens | |
| 7,351,367 B2 | 4/2008 | Swanson, Sr. | |
| 7,427,297 B2 | 9/2008 | Patterson et al. | |
| 7,427,298 B1 | 9/2008 | Swanson, Sr. | |
| 7,637,958 B2 | 12/2009 | Coop | |
| 7,771,487 B2 | 8/2010 | Mantelmacher | |
| 8,211,187 B2 | 7/2012 | Slemker et al. | |
| 8,795,385 B2 | 8/2014 | Bache | |
| 8,801,803 B2 | 8/2014 | Song et al. | |
| 9,050,202 B2 | 6/2015 | Bache et al. | |
| 9,198,778 B2 | 12/2015 | Celebi et al. | |
| 9,248,033 B2 | 2/2016 | Bache | |
| 2001/0005798 A1 | 6/2001 | Caspers | |
| 2001/0016781 A1 | 8/2001 | Caspers | |
| 2002/0040248 A1 | 4/2002 | Karason | |
| 2002/0087215 A1 | 7/2002 | Caspers | |
| 2002/0091449 A1 | 7/2002 | Caspers et al. | |
| 2002/0099450 A1 | 7/2002 | Dean, Jr. et al. | |
| 2003/0144744 A1 | 7/2003 | Grubbs | |
| 2003/0191539 A1 | 10/2003 | Caspers | |
| 2004/0030410 A1 | 2/2004 | Wagman | |
| 2004/0030411 A1 | 2/2004 | Caspers | |
| 2004/0098136 A1 | 5/2004 | Caspers | |
| 2004/0122528 A1 | 6/2004 | Egilsson | |
| 2004/0143345 A1 | 7/2004 | Caspers | |
| 2004/0167638 A1 | 8/2004 | Caspers | |
| 2004/0181290 A1 | 9/2004 | Caspers | |
| 2004/0236434 A1 | 11/2004 | Carstens | |
| 2004/0243251 A1 | 12/2004 | Carstens | |
| 2005/0244220 A1 | 11/2005 | Ingimarsson | |
| 2007/0055383 A1 | 3/2007 | King | |
| 2011/0307080 A1 | 12/2011 | Perkins et al. | |
| 2012/0310371 A1 | 12/2012 | Bachus et al. | |
| 2013/0173020 A1 | 7/2013 | Slemker et al. | |
| 2013/0195540 A1 | 8/2013 | Wozencroft et al. | |
| 2013/0282143 A1 | 10/2013 | Perkins et al. | |
| 2015/0230945 A1 | 8/2015 | Bache et al. | |
| 2016/0000584 A1 | 1/2016 | Brown | |
| 2016/0038314 A1 | 2/2016 | Kuiken et al. | |
| 2016/0120665 A1 | 5/2016 | Muller | |
| 2016/0331562 A1 | 11/2016 | Bache et al. | |
| 2018/0221178 A1 | 8/2018 | Steinberg et al. | |
| 2020/0222211 A1 * | 7/2020 | Hannesson | A61F 2/80 |

FOREIGN PATENT DOCUMENTS

| | | |
|---|---|---|
| DE | 813190 C | 7/1949 |
| DE | 1795809 U | 9/1959 |
| DE | 2060239 A1 | 7/1972 |
| DE | 2540138 A1 | 3/1977 |
| DE | 2729800 A1 | 1/1979 |
| DE | 3221920 A1 | 4/1983 |
| DE | 3508919 A1 | 9/1986 |
| DE | 9419208 U1 | 1/1995 |
| DE | 202005018109 U1 | 3/2006 |
| GB | 267988 A | 9/1925 |
| GB | 2069847 A | 9/1981 |
| GB | 2087727 A | 6/1982 |
| GB | 2338899 A | 1/2000 |
| GB | 2479532 A | 10/2011 |
| JP | 07-155343 A | 6/1995 |
| NL | 2010991 C | 12/2014 |
| RU | 2079292 C1 | 5/1997 |
| WO | 0074611 A2 | 12/2000 |
| WO | 0154631 A1 | 8/2001 |
| WO | 03024367 A2 | 3/2003 |
| WO | 03024370 A1 | 3/2003 |
| WO | 03039398 A1 | 3/2003 |
| WO | 03099173 A1 | 12/2003 |

OTHER PUBLICATIONS

2nd Office Action (and English Translation) of Chinese Patent Application No. 201480010447.5, dated Aug. 26, 2016.

Ossur, Icelock clutch 4H 214 L-214000, Instructions for Use, 3 pages.

Ossur, Icelock(r) 200 Series, Product Information, Mar. 1, 2004, 2 pages, http://www.ossur.com/print.asp?PageID=147&Redirect=False &search_string=&newsid=. . . .

Ossur, Socket Adapters, Product Information, Mar. 1, 2004, 5 pages, http://www.ossur/com/print.asp?PageID=189&Redirect=False&search_string=&newsid=. . . .

Ossur "Icelock 211 Lamination Procedure—EB345/1 JG," Technical Manual, Mar. 2003, 18 pages.

Metric Roller Clutches, https://www.sdp-si.com/ss/pdf/sscr7002.pdf.

\* cited by examiner

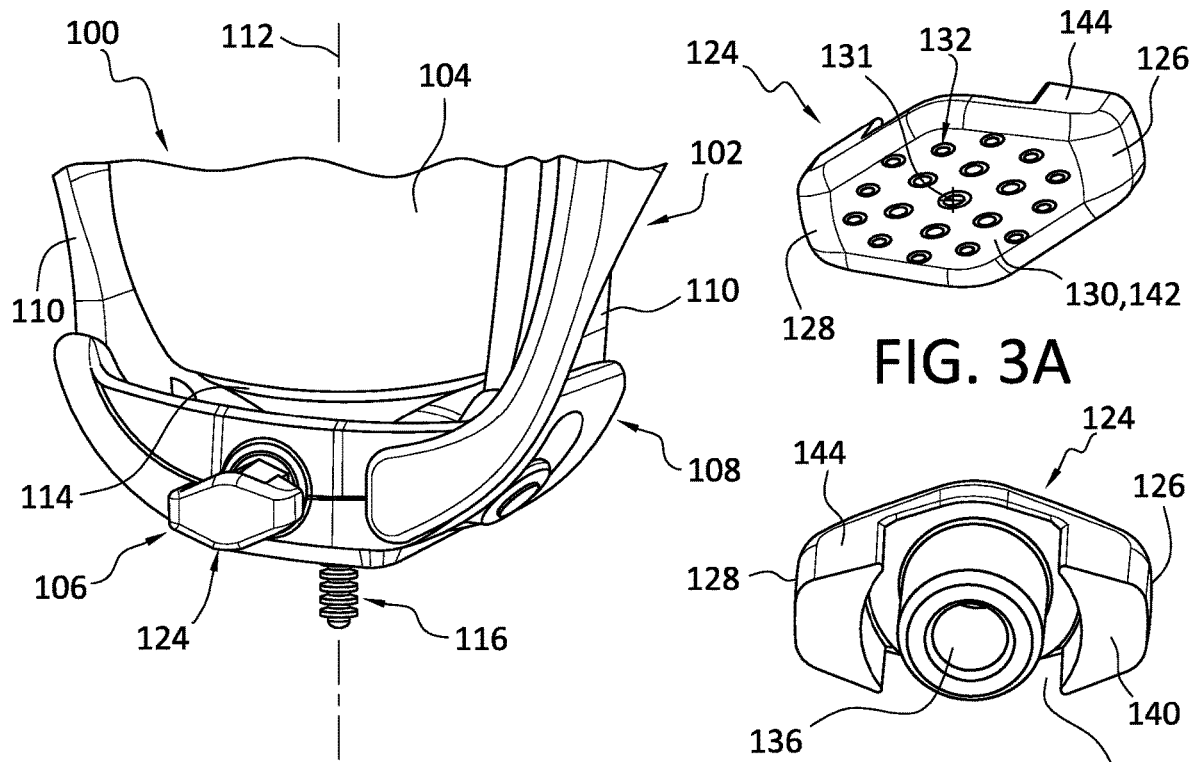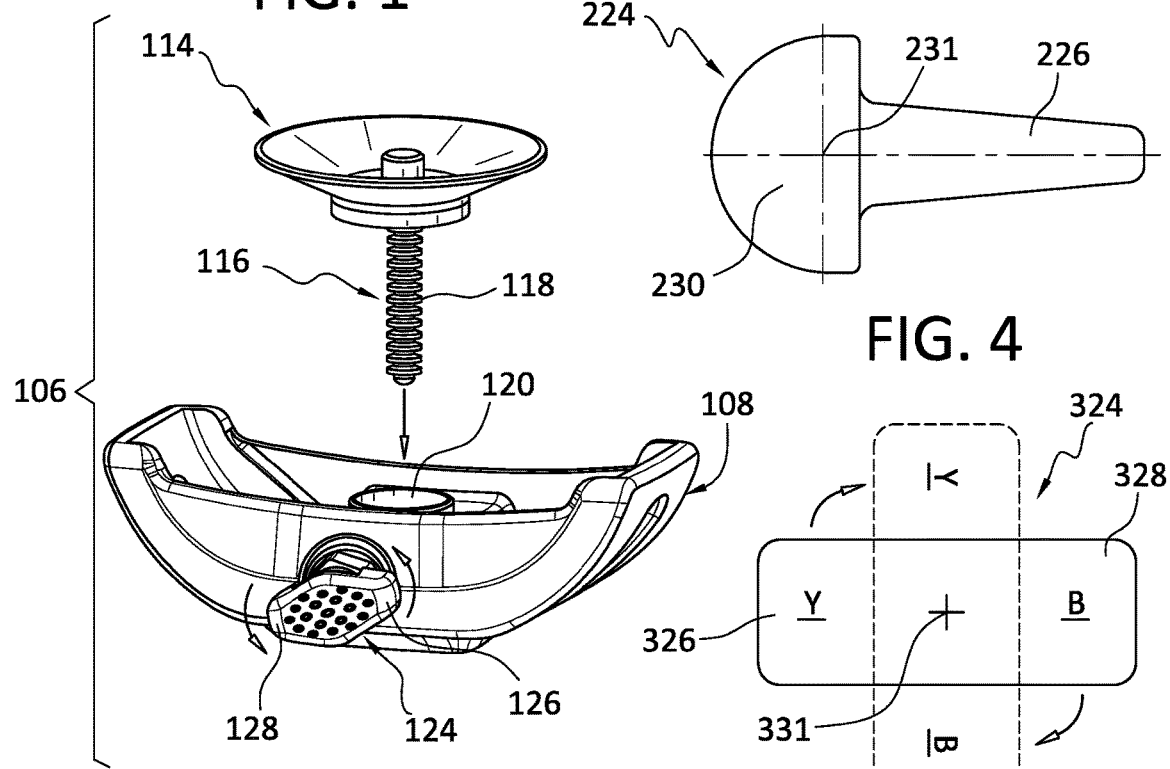

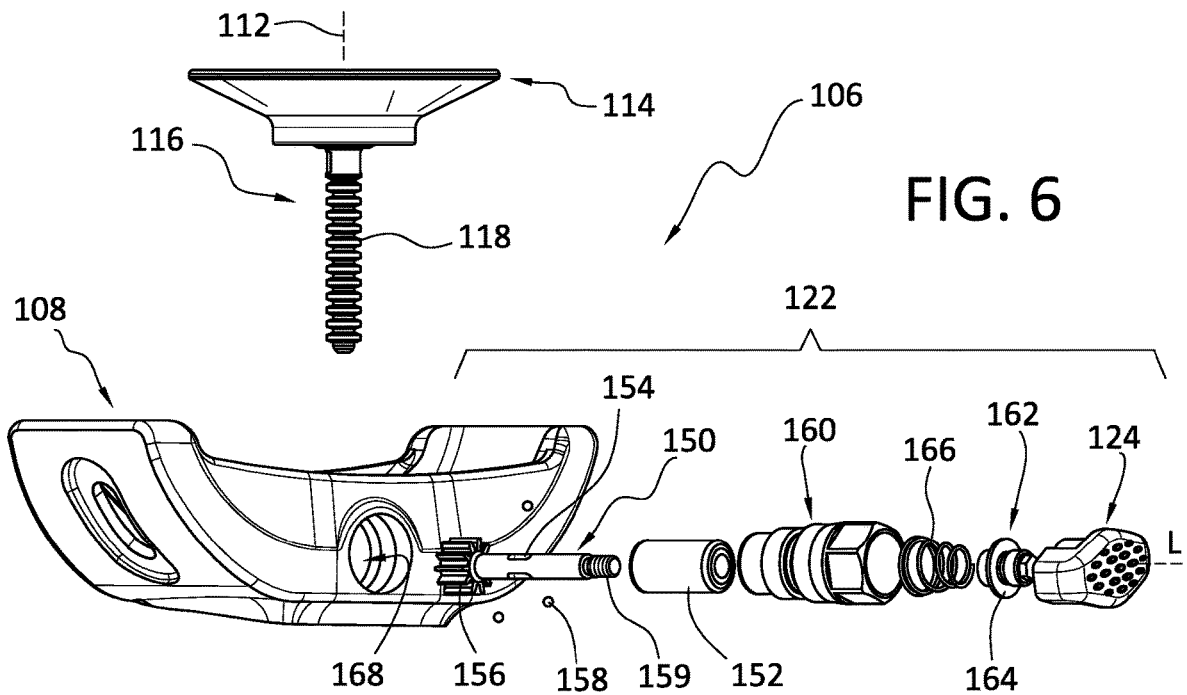
FIG. 6
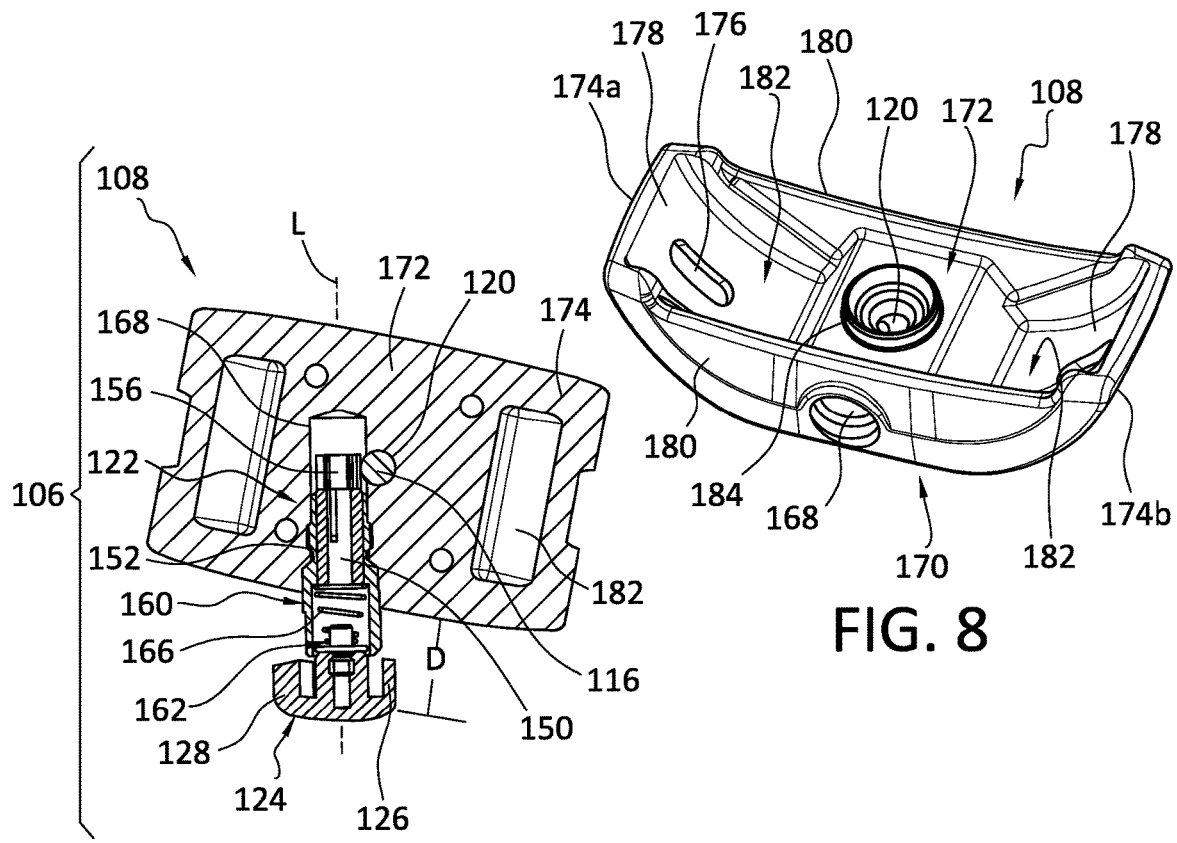
FIG. 7
FIG. 8

PROSTHETIC ATTACHMENT SYSTEM AND CORRESPONDING LOCK ASSEMBLY

TECHNICAL FIELD

This disclosure is directed to a prosthetic attachment system, and in particular to a lock assembly for locking a prosthetic liner to a prosthetic socket.

BACKGROUND

A typical prosthetic leg and foot include a socket, pylon, and foot. A socket is the portion of a prosthesis that fits around and envelops a residual limb or stump, and to which prosthetic components, such as a foot, are attached. The socket must fit closely to the residual limb to provide a firm connection and support, but must also be sufficiently loose to allow for circulation. Combined with proper fitting, the socket transfers loads from the residual limb to the ground in a comfortable manner.

A prosthetic liner is arranged as an interface between the socket and the residual limb to increase comfort. Generally, the prosthetic liner includes an elastomeric body having a closed distal end and an open proximal end pulled or rolled over the residual limb. The prosthetic liner adheres to the residual limb surface and acts as an interface between the residual limb and the socket by extending between and facilitating contact between the residual limb and the rigid components of the socket.

Different mechanisms exist for holding the socket on the residual limb during use of the prosthesis. For instance, locking pin-type systems provide an attachment pin at the closed distal end of the prosthetic liner that engages a prosthetic-system lock assembly at the distal end of the socket. The lock assembly is connected to the components, such as the pylon, connecting to the foot and effectively couples the liner, the socket, and the components together. An unlocking mechanism can release the attachment of the prosthetic liner to the socket.

A problem inherent in conventional locking pin-type systems is that they incorrectly lock if a user does not properly insert the attachment pin in the lock assembly. This problem can cause the failure of the lock assembly during use and significant injury to the user. Too much free play between the attachment pin and the lock assembly can cause a slack connection, so that the residual limb undesirably moves up and down within the socket when the user is walking, an undesirable phenomenon known as "pistoning." The free play may also lead to premature wear of the attachment pin and lock components which can cause a failure of the lock.

Conventional lock assemblies are also known to make donning and doffing of the residual limb in the socket problematic. This problem is especially evident for elderly users and others who commonly have difficulty properly locating the attachment pin in the lock assembly due to limited cognition, limited dexterity, or poor eyesight There is a need for a prosthetic attachment system that makes donning and doffing of prosthetic socket easier and more intuitive, and which minimizes pistoning and incorrect locking of the system.

SUMMARY

The disclosure describes various embodiments of a prosthetic attachment system, particularly including a lock assembly for a prosthetic system, providing construction and design that facilitates a more intuitive and secure connection between a residual limb and a prosthetic socket.

A lock assembly embodiment according to the disclosure is arranged for connecting a distal end of a prosthetic liner to a distal end of a prosthetic socket. The lock assembly includes a base arranged to be supported by or at the distal end of the prosthetic socket, and defines a pin bore. An attachment pin is arranged to be carried by the prosthetic liner proximate the distal end and insertable through the pin bore. A lock mechanism is arranged to be carried by the base and rotatable about a rotation axis. The lock mechanism includes a control knob extending outwardly from a side of the base and has at least one elongate projection extending in a direction transverse relative to the rotation axis. The attachment pin is arranged to interact with the lock mechanism as the attachment pin moves distally through the pin bore, and causes the control knob to spin the at least one projection about the rotation axis.

The lock assembly may be provided as a kit for being added, for example retroactively or for retrofitting, to a socket and liner, or the socket and liner may be provided with a lock assembly according to the disclosure. More broadly, a prosthetic attachment system comprises the socket, liner, and the lock assembly, enabling improved and more intuitive attachment when the socket and liner have such corresponding and interacting components.

When a user correctly pushes the attachment pin into the pin bore, the user can see and/or feel the at least one elongate projection of the control knob spinning. This advantageously provides a clear indicator or feedback to the user that the attachment pin is correctly pushed into the pin bore of the base. This is beneficial when donning or doffing the socket for users with limited cognition, limited dexterity, and/or poor eyesight.

The at least one elongate projection of the control knob stops spinning once the attachment pin is fully inserted or inserted to a predetermined extent in the pin bore of the base. This observable change in the action of the control knob has the effect of providing another clear indicator that the attachment pin is securely and fully inserted in the lock mechanism, which, in turn, reduces the likelihood of a user only partially inserting the attachment pin in the prosthetic lock assembly. This is advantageous because incomplete or partial insertion of the attachment pin in the pin bore could result in failure of the lock between the attachment pin and the lock mechanism and/or significant injury to the user.

To verify that the attachment pin is fully engaged with the lock mechanism, the user can grasp the at least one elongate projection to turn the control knob in the same direction as it was spinning during insertion of the attachment pin in the pin bore. If the user is unable to turn the control knob, the attachment pin is fully engaged with the lock mechanism. If the user can turn the control knob, the rotation of the control knob is configured and arranged to draw the attachment pin further into the pin bore until it is fully engaged.

The combination of the control knob and the lock mechanism can thus make donning and doffing of the socket easier and minimize incorrect attachment of the prosthetic socket system components by a user.

BRIEF DESCRIPTION OF THE DRAWINGS

These and other features, aspects, and advantages of the present disclosure will become better understood regarding the following description, appended claims, and accompanying drawings.

FIG. 1 is a partial side perspective view of a prosthetic attachment system having a lock assembly according to the disclosure.

FIG. 2 is a perspective view of the lock assembly in FIG. 1.

FIG. 3A is a front perspective view of the control knob in FIG. 1.

FIG. 3B is a rear perspective view of the control knob in FIG. 1.

FIG. 4 is a perspective view of a control knob according to another embodiment of a prosthetic attachment system.

FIG. 5 is a front perspective view of a control knob according to another embodiment of a prosthetic attachment system.

FIG. 6 is an exploded view of the lock assembly in FIG. 1.

FIG. 7 is a cross-sectional view of the lock assembly of FIG. 1 in the prosthetic attachment system.

FIG. 8 is a top perspective view of the base in FIG. 1 according to an embodiment.

Figure 9:
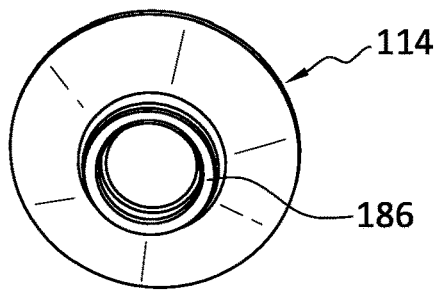
FIG. 9 is a bottom view of an umbrella according to an embodiment of a prosthetic attachment system.

The drawing figures are not necessarily drawn to scale, but instead are drawn to provide a better understanding of the components, and are not intended to be limiting in scope, but to provide exemplary illustrations. The figures illustrate exemplary configurations of prosthetic attachment systems including lock assemblies, and in no way limit the structures or configurations of a prosthetic attachment system and components thereof including prosthetic attachment systems and corresponding lock assemblies according to the present disclosure.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

Embodiments of the present disclosure advantageously provide a prosthetic attachment system and corresponding lock assembly that facilitates a more intuitive and secure connection between a residual limb and a prosthetic socket. FIG. 1 illustrates a prosthetic socket system 100 according to an embodiment including a socket 102, a prosthetic liner 104, and a lock assembly 106. The lock assembly 106 may be provided as a kit of components provided interchangeably together, or as individual components forming part of the socket 102 or the prosthetic liner 104.

In the illustrated embodiment, the socket 102 comprises an adjustable socket including a base 108 and a plurality of longitudinal supports 110 connected to the base 108 and distributed about a longitudinal axis 112 of the socket 102. The socket 102 can include a plurality of shell components connected to the longitudinal supports 110 that collectively form a socket wall defining a receiving volume adapted to receive a residual limb and a prosthetic liner worn thereon. The base 108 is configured to provide support for a distal end of the residual limb and can comprise at least part of the lock assembly 106 for fixing or securing the residual limb or the prosthetic liner 104 to the socket 102. The base 108 defines a pin bore 120 generally centrally disposed relative to and within the base 108.

The socket 102 is radially adjustable between an open configuration and a closed configuration. In the open configuration, at least some of the longitudinal supports 110 and/or shell components may move or are forced radially outward relative to the longitudinal axis 112, increasing the receiving volume and/or increasing the circumference of the socket 102. This effectively loosens the fit of the socket 102 on a residual limb inserted in the receiving volume and/or decreases the loading on the residual limb from the socket wall or the longitudinal supports 110. In the closed configuration, at least some of the longitudinal supports 110 and/or shell components are moved or forced radially inward relative to the open configuration, decreasing the receiving volume or decreasing the circumference of the socket 102. This may be particularly advantageous for donning and doffing, as the open configuration facilitates easier insertion and removal of the limb residuum and the prosthetic liner 104.

A tensioning system can be arranged to selectively secure a residual limb within the receiving volume by moving the socket 102 between the open/expanded and closed configurations. Other examples and additional details of suitable prosthetic sockets are included in U.S. Pat. No. 8,795,385, granted Aug. 5, 2014, U.S. Pat. No. 9,248,033, granted Feb. 2, 2016, U.S. Pat. No. 9,050,202, granted Jun. 9, 2015, U.S. Pat. No. 9,962,273, granted May 8, 2018, U.S. Patent Application Publication 2015/0230945, published Aug. 20, 2015, and U.S. Patent Application Publication 2018/0221178, published Aug. 9, 2018, each of which is incorporated by reference in its entirety. While the socket 102 is described as an adjustable socket, in other embodiments, the socket 102 can comprise a conventional static socket devoid of adjustability. The foregoing references are merely exemplary, and the socket 102 may have any suitable construction, operation, or configuration.

An exemplary prosthetic liner can be found in U.S. Pat. No. 4,923,474, granted May 8, 1990, U.S. Pat. No. 6,136,039, granted Oct. 24, 2000, and U.S. Pat. No. 6,485,776, granted Nov. 26, 2002, each of which is incorporated by reference in its entirety. The foregoing references are merely exemplary, and the liner 104 may have any suitable construction, composition, or configuration.

The prosthetic liner 104 is configured to be donned on the residual limb and positioned in the socket 102. Typical liners are made of soft, stretchable material and protect the residual limb and act as an interface between the socket 102 and the skin of the residual limb. The prosthetic liner 104 generally includes a liner body having a proximal end, which is open, and a distal end, which is closed. The liner body defines an inner surface that interfaces with the skin, and an outer surface opposing the inner surface. The liner body can be formed of a polymeric or elastomeric material like silicone, copolymer gel, polyurethane, combinations thereof, or any other suitable material.

The distal end of the prosthetic liner 104 may include an umbrella 114 that enables interconnection between the prosthetic liner 104 and the socket 102. The umbrella 114 generally comprises an umbrella-shaped base and a neck that depends from the center of the base. An internally threaded center bore is formed in the neck.

An attachment pin 116 is secured to the distal end of the prosthetic liner 104. The attachment pin 116 may be mounted to the prosthetic liner 104 by being molded or threaded onto the distal end of the prosthetic liner 104. In the illustrated embodiment, the attachment pin 116 can be threaded into the internally threaded center bore of the umbrella 114. The attachment pin 116 is positioned to extend through the pin bore 120 of the base 108 and thus through the distal end of the socket 102. The attachment pin 116 includes a plurality of notches 118 formed along a longitudinal length thereof. The notches 118 are preferably axially spaced and define a curved configuration in axial cross-section. The attachment pin 116 can include an upper shank portion arranged for attachment to the prosthetic liner 104.

A lock mechanism 122 (shown in FIG. 6) of the lock assembly 106 is positioned in the base 108 to engage and secure the attachment pin 116 within the base 108. The lock mechanism 122 is configured and arranged to engage the attachment pin 116 with the lock mechanism 122 interacting with the notches 118 of the attachment pin 116. It will be appreciated that the lock mechanism 122 can comprise any suitable lock mechanism. Other exemplary lock mechanisms are described in U.S. Pat. No. 7,217,060, granted May 15, 2007, owned by the assignee of this disclosure and incorporated herein in its entirety by reference.

The lock assembly 106 includes a control knob 124 operably coupled to the lock mechanism 122. According to the present disclosure, the control knob 124 is arranged and configured to make donning and doffing of a prosthetic socket 102 easier, and to minimize incorrect locking of the attachment pin 116 in the lock mechanism 122. For instance, the control knob 124 can comprise a button protruding a distance outwardly from a side of base 108, and having an oversized configuration such as defining a pair of projections 126, 128, each being elongate in form.

The lock mechanism 122 and the notches 118 of the attachment pin 116 can operate to spin or rotate the control knob 124 about a rotation axis 131. For instance, as the attachment pin 116 is being inserted through the pin bore 120 in the base 108, the interaction between the lock mechanism 122 and the notches 118 of the attachment pin 116 spins the control knob 124 about the rotation axis 131.

When a user is correctly pushing the attachment pin 116 distally or downwardly into the pin bore 120 of the base 108, the user can see and/or feel the projections 126, 128 of the control knob 124 spinning. This advantageously provides a clear indicator or feedback to a user that the attachment pin 116 is being correctly inserted into the pin bore 120 of the base 108. This is beneficial for users with limited cognition, limited dexterity, and/or poor eyesight while donning the socket 102.

The projections 126, 128 of the control knob 124 may stop spinning when the attachment pin 116 is fully inserted or inserted to a predetermined extent in the pin bore 120 of the base 108. This observable change in the action of the control knob 124 provides another indicator that the attachment pin 116 is securely and fully inserted in the lock mechanism 122, which prevents a user from only partially inserting the attachment pin 116 in the lock assembly 106. This is advantageous because incomplete or partial insertion of the attachment pin 116 could cause failure of the lock between the attachment pin 116 and the lock mechanism 122, accelerated wear of the components, and/or significant injury to the user.

To verify that the attachment pin 116 is engaged with the lock assembly 106, the user can grasp the projections 126, 128 to turn the control knob 124 in the same direction as it was spinning during insertion of the attachment pin 116 in the pin bore 120. If the user cannot turn the control knob 124, the attachment pin 116 is fully engaged with the lock mechanism 122. If the user can turn the control knob 124, the rotation of the control knob 124 is configured and arranged to draw the attachment pin 116 into the lock assembly 106 until it is fully engaged.

When it is desired to remove the attachment pin 116 from the base 108, the control knob 124 is configured so a user can push the control knob 124 inwardly to disengage the lock mechanism 122 from the attachment pin 116. The attachment pin 116 may be freely withdrawn from the base 108 upon disengagement of the lock mechanism 122 from the attachment pin 116. The combination of the control knob 124 and the lock mechanism 122 thus makes donning and doffing of the socket 102 easier and minimizes incorrect locking of the prosthetic socket system 100 by a user.

FIGS. 3A and 3B illustrate the control knob 124 in additional detail according to an embodiment. The control knob 124 can have a body defining an inner surface 140 arranged to engage and/or face the base 108, an outer surface 142 opposite the inner surface 140, and side surfaces 144 extending between the inner and outer surfaces 140, 142. The periphery of the outer surface 142 can define rounded or curved edges, improving the feel and ergonomics of the control knob 124. The body of the control knob 124 can be formed of plastic, rubber, foam, carbon fiber, metal, combinations thereof, or any other material which would provide enough strength to resist undesirable deformation during use. In an embodiment, the body can have a rigid configuration with an overmold having a flexible configuration applied thereto for enhanced grip and comfort, and without compromising on or sacrificing overall structural strength.

The projections 126, 128 extend in opposite directions along a longitudinal length of the body from a central portion 130 of the body. The projections 126, 128 may define an elongate configuration of the control knob 124. The control knob 124 is shown having a generally trapezoidal shape but can have any suitable shape. The projections 126, 128 provide enhanced visual and/or tactile indicators to a user about the engagement of the attachment pin 116 with the lock mechanism 122. In addition, the orientation and arrangement of the projections 126, 128 provide a large ergonomic gripping area for the user, making operation of the control knob 124 easier for users with limited dexterity.

For instance, the side surfaces 144 of the projections 126, 128 can provide additional gripping area for a user's thumb and fingers when turning the control knob 124. The projections 126, 128 are shown having the same shape and being generally symmetrically arranged but in other embodiments the projections 126, 128 can have different shapes and/or may be arranged in asymmetric configurations. For instance, one projection can have a round shape and the other projection can have a rectangular shape, helping to accentuate the spinning of the projections 126, 128 for a user.

The outer surface 142 can include at least one textured region 132 configured to improve grip and/or provide tactile feedback for a user, making it easier for a user with poor eyesight to locate the control knob 124 on the base 108. The textured region 132 can comprise different patterns of protrusions and/or recesses formed along the outer surface 142. For example, the textured region 132 can comprise a plurality of recesses distributed on the central portion 130, each defining a longitudinal length generally aligned with the longitudinal length of the control knob 124 so a user can observe or touch along the longitudinal lengths of the recesses to help determine the orientation of the control knob 124. The depicted embodiment is merely exemplary, and the textured region 132 and protrusions or recesses may have any suitable configuration.

The inner surface 140 of the control knob 124 can be contoured to generally correspond to a contour of the side of the base 108. This can allow the control knob 124 to form a lower profile fit between the control knob 124 and the base 108. The inner surface 140 can also provide a support area for the control knob 124 against the base 108 if the control knob 124 engages with the base 108 when the control knob 124 is pushed in.

As seen in FIG. 3B, a cylindrical portion defining a bore 136 is on the inner surface 140 of the control knob 124 and is configured and arranged to facilitate a connection between the control knob 124 and the lock mechanism 122. The control knob 124 can rotate about a rotation axis 131 defined at this connection. In an embodiment, the bore 136 can include internal threads along a length thereof configured to form a threaded connection between the control knob 124 and the lock mechanism 122. Optionally, the body can include a gap 146 surrounding the cylindrical portion. This gap 146 can reduce the weight of the control knob 124.

According to a variation, the control knob 124 can be provided with a unique indicator (e.g., a double click, light, or vibration) when the attachment pin 116 is fully engaged with the lock mechanism 122, helping a user determine when the socket 102 is safely secured to the residual limb. This advantageously improves ease of use and helps reduce injury to the user. In other embodiments, the control knob 124 can include a counting unit configured to count and display to the user how many revolutions the control knob 124 has completed after the attachment pin 116 in inserted into the pin bore 120. In embodiments, the control knob 124 may be configured with a power supply, a sensor, a processor, and a transmitter to communicate with a mobile device and to indicate that the attachment pin 116 is fully engaged, mitigating a need to physically watch the control knob 124 spin or rotate.

FIG. 4 illustrates a control knob 224 according to another embodiment. As in the previous embodiment, the control knob 224 is arranged and configured to makes donning and doffing of the socket 102 easier, and to minimize incorrect locking of the attachment pin 116 in the lock mechanism 122. The control knob 224 includes a body having an irregular shape defining an oversized head portion 230 including a rotation axis 231 and a single projection 226 extending from the head portion 230 in a direction traversing the rotation axis 231. The rotation axis 231 can be defined by a connection between the control knob 224 and the lock mechanism 122.

The projection 226 can have a width that tapers in a direction away from the head portion 230 and is arranged and configured so a user can see and/or feel the projection 226 spinning when the user is correctly pushing the attachment pin 116 into the base 108, reducing the risk of the user incorrectly donning the socket 102. In addition, the orientation and arrangement of the projection 226 provides a large ergonomic gripping area for the user, making manual operation of the control knob 224 easier for users with limited dexterity, such as by increasing a user's leverage when manipulating the control knob 224.

FIG. 5 illustrates yet another embodiment of a control knob 324 arranged and configured to make donning and doffing of the socket 102 easier and safer. The control knob 324 can be configured similar to the foregoing embodiments, and may include a body having an elongate configuration and a rotation axis 331. A longitudinal length of the body extends in a direction traversing the rotation axis 331. The rotation axis 331 can be defined by a drive shaft of the lock mechanism or a connection between the control knob 324 and the lock mechanism 122. The control knob 324 can include a first part 326 comprising a first projection and a second part 328 comprising a second projection extending in opposite directions traversing the rotation axis 331.

Each part 326, 328 can have a different colored region. This advantageously can help accentuate the spinning of the projections or parts for a user. For instance, the first part 326 can be colored yellow Y and the second part 328 can be colored blue B so a user can more easily see that the parts 326, 328 or body is spinning when the user is correctly pushing the attachment pin 116 into the base 108 due to the alternating positions of the blue B and yellow Y regions. The depicted embodiment is merely exemplary, and any suitable configuration of colors, shapes, materials, or components may be utilized.

FIGS. 6 and 7 illustrate the lock mechanism 122 in greater detail according to an embodiment. The lock mechanism 122 is located inside of the base 108 of the socket 102 and comprises a shaft 150 for engaging the attachment pin 116, a sleeve assembly 152 encompassing at least a portion of the shaft 150, a bearing-and-groove arrangement 154 providing cooperative movement between the sleeve assembly 152 and the shaft 150, and a clutch device 160 arranged to securely receive the sleeve assembly 152 and permit smooth and/or generally uniform rotation of the shaft 150 and the sleeve assembly 152, and consequently the control knob 124.

The shaft 150, the sleeve assembly 152, and the clutch device 160 generally extend along a common axis L, which may be the axis of rotation 131 or may be a different axis. By extending commonly along the axis of rotation 131, the shaft 150, the sleeve assembly 152, the clutch 160, and the control knob 124 can rotate uniformly to provide indicia to a user that the attachment pin 116 is being properly inserted into the pin bore 120 for effective and intuitive attachment of the components of the prosthetic attachment system 100.

The shaft 150 includes an engaging member 156, located at a first end, such as a pinion, a threaded portion 159 located at a second end thereof, and a central portion interposed between the pinion 156 and the threaded portion 159. The pinion 156 is configured and arranged to operably communicate with the pin bore 120 and to engage the attachment pin 116 so teeth of the pinion 156 can mesh or engage with the notches 118 of the attachment pin 116. The pinion 156 may be formed integrally with the shaft 150, or the pinion 156 may be attached to the shaft 150. The teeth of the pinion 156 may correspond in size and configuration to the configuration of the notches 118 of the attachment pin 116.

The shaft 150 defines at least one groove 154 longitudinally extending along the central portion of the shaft 150. The at least one groove 154 preferably has a depth with contours sufficient to accommodate at least a portion of at least one ball bearing 158. The sleeve assembly 152 defines along its interior surface at least one groove located at or near a first end portion intended to be near or adjacent to the pinion 156. The sleeve assembly 152 is positioned on the shaft 150 so the grooves of the sleeve assembly 152 are aligned with the at least one groove 154 of the shaft 150, with a groove 154 of the shaft 150 and a corresponding groove of the sleeve assembly 152 defining a pair of mutually opposed grooves.

The at least one ball bearing 158 is seated in one of the pairs of mutually opposed and corresponding grooves of the shaft 150 and the sleeve assembly 152, respectively. Preferably a plurality of ball bearings 158 are provided, with at least one ball bearing 158 corresponding to each of the pairs of mutually opposed grooves. The at least one ball bearing 158 is configured to permit movement or translation of the shaft 150 along the longitudinal axis L relative to the sleeve assembly 152, and may be configured to prohibit rotation of the shaft 150 relative to the sleeve assembly 152. It will be understood that different bearing elements, such as cylinders, may be provided in place of ball bearings in the passageways formed by the grooves.

Preferably, the grooves are configured to permit the shaft 150 to move within the sleeve assembly 152 a distance until the pinion 156 completely disengages from the notches 118 of the attachment pin 116, permitting the attachment pin 116 to be freely removed from the lock mechanism 122 without impediment.

The sleeve assembly 152 is securely received for rotation in one direction within the one-way clutch device 160. For instance, the sleeve assembly 152 can be secured within a first bore portion of the clutch device 160 by rollers (not shown) arranged about the inner periphery of the clutch device 160. When the sleeve assembly 152 is rotated in a first direction, the rollers are configured within the first bore portion to wedge against or contact the outer periphery of the sleeve assembly 152 to prevent further rotation of the sleeve assembly 152.

As taught in U.S. Pat. No. 7,217,060, the rollers may be those found in a conventional unidirectional or one-directional roller clutch such as a roller clutch produced by Stock Drive Products of New Hyde Park, N.Y. under catalog number 599NH3MURCO406.

When the sleeve assembly 152 is rotated in a second or opposite direction, the rollers freely rotate against the sleeve assembly 152. It will be understood that the permitted rotational direction of the sleeve assembly 152 within the clutch device 160 corresponds to the rotational direction in which the pinion 156 of the shaft 150 drives the attachment pin 116 into the base 108. The clutch device 160 may include a plurality of external threads arranged for engaging a plurality of internal threads of a transverse bore 168 defined by and within a thickness of the base 108.

The threads of the clutch device 160 and the transverse bore 168 may advantageously facilitate rotation of the lock mechanism 122 about the rotation axis 131 while preventing disengagement of the lock mechanism 122 from the base 108. As depicted in FIG. 7, the transverse bore 168 may extend generally obliquely relative to the bore 120 so as to facilitate optimal contact between the attachment pin 116 and the lock mechanism 122, with the lock mechanism 122 operably communicating with the bore 120 and the attachment pin 116.

A coupler 162 includes a first end arranged to couple with the drive shaft 150, and second end arranged to couple with the control knob 124, and a radially extending flange 164 defined between the first and second ends. It will be appreciated that the coupler 162 can be coupled to the drive shaft 150 and the control knob 124 in any suitable manner. A resilient member 166 such as a spring is configured to engage between the flange 164 and a seat flange of the clutch device 160.

The control knob 124 can be connected to the second end of the coupler 162. The lock mechanism 122 is configured so that depression of the control knob 124 inwardly or towards the base 108 urges travel of the drive shaft 150 along the longitudinal axis L, and rotation of either the drive shaft 150 or the control knob 124 rotates the other in the direction permitted by the clutch device 160.

FIG. 7 shows the attachment pin 116 positioned within the pin bore 120 of the base 108 and engaged with the pinion 156 of the drive shaft 150. As seen, the resilient member 166 can bias the drive shaft 150 into the position wherein the pinion 156 engages the notches 118 of the attachment pin 116. In the position shown in FIG. 7, distal or downward movement of the attachment pin 116 through the pin bore 120 rotates the pinion 156 and the drive shaft 150 in the direction permitted by the clutch device 160, which, in turn, spins the projections 126, 128 of the control knob 124 extending a distance D from the side of the base 108.

A user can see the projections 126, 128 spinning, providing a clear indictor to the user that the attachment pin 116 is being correctly pushed into the lock mechanism 122. The distance D may be selected such that the projections 126, 128 can spin without interference from the base 108. The longitudinal axis L of the lock mechanism 122 may be arranged obliquely relative to the base 108, and/or the projections 126, 128 may be arranged to extend obliquely by the distance D relative to the base 108.

When the projections 126, 128 of the control knob 124 stop spinning, the user can easily grasp the large gripping area provided by the projections 126, 128 to turn the control knob 124 in the same direction as it was spinning. If the user cannot turn the control knob 124, the attachment pin 116 is fully and safely engaged with the lock mechanism 122. If the user can turn the control knob 124, the manual rotation of the control knob 124 by the user is configured to draw the attachment pin 116 into the lock mechanism 122 until it is fully and safely engaged by the engagement between the pinion 156 of the drive shaft 150 and the teeth or pegs 118 of the attachment pin 116.

When it is desired to remove the attachment pin 116 from the base 108, the control knob 124 can be configured so a user can push the control knob 124 inwardly to disengage the lock mechanism 122 from the attachment pin 116. The outer surface of the central portion 130 of the control knob 124 can provide a large and substantially flat surface. This advantageously makes it easier and more comfortable to push the control knob 124 inwardly. The attachment pin 116 may be freely withdrawn from the base 108 upon disengagement of the lock mechanism 122 from the attachment pin 116 as the pinion 156 is translated deeper within the transverse bore 168.

The control knob 124 of the present disclosure in combination with the lock mechanism 122 thus makes donning and doffing of the socket 102 easier and minimizes incorrect locking of the prosthetic socket system 100.

The lock mechanism 122 is nearly entirely located in the base 108 of the socket 102 eliminating the use of a conventional lock body which is typically located below the distal surface of the socket. This advantageously reduces the weight, complexity, and cost of the prosthetic socket system 100.

Referring to both FIGS. 7 and 8, the base 108 connects the longitudinal supports 110 (shown in FIG. 1) and is configured to provide support for a distal end of the residual limb.

The base 108 comprises a body 170 having a main portion 172 and a connecting portion 174 having first and second connection portions 174a, 174b extending outwardly and upwardly from a lower region of the main portion 172. The base 108 can be formed of any suitable material such as plastic, metal, carbon fiber, or combinations thereof.

The upper surface of the connecting portions 174a, 174b defines a seat 178 arranged to generally correspond to the configuration of a distal end portion of the longitudinal support 110. In an embodiment, the seat 178 defines a curvature generally corresponding to a curvature to an outer surface of the distal end portion of the longitudinal support 110 such that as the distal end portion is moved up and down on the seat 178, the angle of the longitudinal support 110 varies. The curvature and/or length of the seat 178 can define a range of angular adjustments for the longitudinal support 110. Each connecting portion 174a, 174b defines at least one elongated opening 176 arranged to receive fasteners for attaching the longitudinal supports 110 to the base 108.

The base 108 further includes a pair of wall segments 180 separated from one another by the main portion 172 and extending between and connecting the connecting portions 174a, 174b. The wall segments 180 both provide reinforcement and help resist movement of the connecting portions 174 relative to one another. The walls 180 further help protect the distal end portion of the longitudinal supports 110 and the main portion 172 and restrict side to side movement of the distal end portion of the longitudinal supports 110 on the base 108. Open areas 182 are formed in the base 108 between the main portion 172 and the connecting portions 174 for accommodating the distal end portions of the longitudinal supports 110. In addition, these open areas 182 beneficially reduce the overall weight and cost of the base 108. The open areas 182 are shown extending partially through the thickness of the base 108 but in other embodiments can extend entirely therethrough.

The main portion 172 extends between the wall segments 180 and defines a thickness between its upper and lower surfaces that is sized to accommodate the lock mechanism 122. The main portion 172 includes the pin bore 120 formed therethrough, and the transverse bore 168 extending therein and intersecting at least a portion of the pin bore 120. In embodiments, the transverse bore 168 extends generally orthogonal through the main portion 172 to the pin bore 120.

An annular flange 184 surrounds the pin bore 120 and extends axially upward from a top of the pin bore 120 as best shown in FIG. 8. The annular flange 184 can include a conical inner surface configured to funnel or guide the attachment pin 116 into the pin bore 120. The annular flange 184 can also be sized to fit within a corresponding annular flange 186 surrounding the opening in the umbrella 114 and extending downward from a bottom of the umbrella 114, as seen in FIG. 9. For instance, the annular flange 184 on the main portion 172 can form a male part configured to closely fit within the annular flange 186 of the umbrella 114 forming a female part when the attachment pin 116 is fully inserted in the pin bore 120.

This arrangement advantageously helps maintain the desired alignment between the base 108 of the socket 102 and the prosthetic liner 104. In addition, it makes donning of the socket 102 easier by helping to align the attachment pin 116 with the pin bore 120. This also helps forgive poor alignment of the prosthetic liner 104 within the socket 102. It will be appreciated that in other embodiments, the annular flange 186 of the umbrella 114 can fit within the annular flange 184 of the main portion 172. In yet other embodiments, the umbrella 114 and main portion 172 can include one or more different alignment features.

Referring to FIG. 8, the main portion 172 is shown having a trapezoidal cross-section, providing a larger base toward the bottom of the base 108 for accommodating the lock mechanism 122 and supporting the distal end of the residual limb. In other embodiments, the main portion 172 can have a rectangular cross section, an elliptical cross section, a square cross section, an irregular cross-sectional shape, or any other suitable cross-sectional shape.

Figure 10:
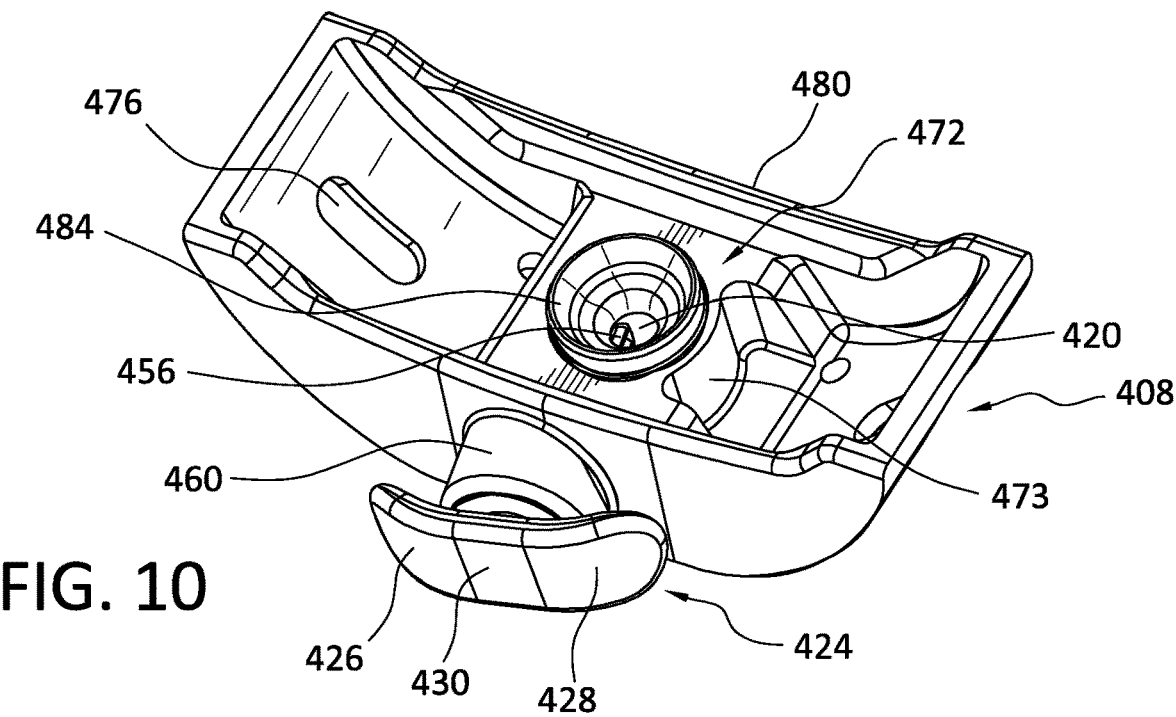
FIG. 10 is a perspective view of another embodiment of a lock assembly.
Figure 11:
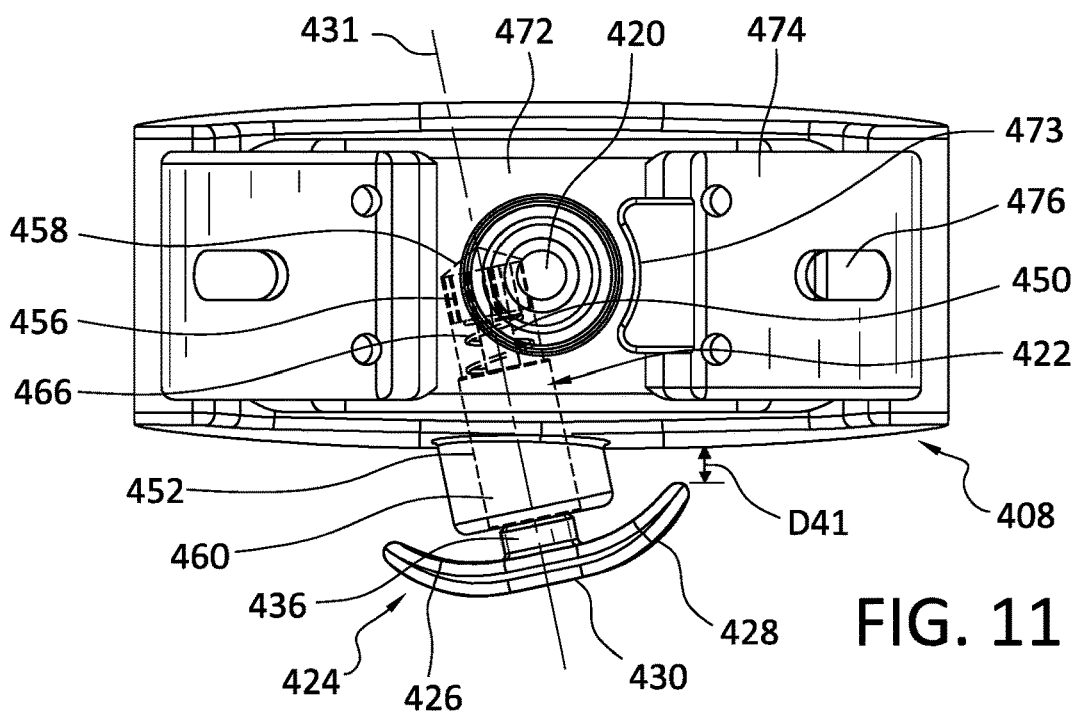
FIG. 11 is a top plan view of the lock assembly of FIG. 10.

In an alternative embodiment shown in greater detail in FIGS. 10 and 11, a control knob 424 may be provided with a lock mechanism 422 similar to the foregoing embodiments. The lock mechanism 422 may be configured to cooperate with the control knob 424 such that, rather than being configured to be pushed or pressed inward by a user in order to disengage or engage the lock mechanism and the pin attachment, the control knob 424 is pulled outwardly by a user in order to engage or disengage the lock mechanism 424 from a pin attachment 116.

The control knob 424, as shown, may be provided with a central portion 430 flanked on opposed sides by first and second projections 426, 428. The first and second projections 426, 428 may be curved inwardly toward the base 408 of the lock assembly, defining a curvature and maintaining a minimized profile. The first and second projections 426, 428 can be configured such that a user can intuitively grasp the first and/or second projections 426, 428 for straightforwardly manipulating the control knob 424, and such that spinning of the control knob 424 as the attachment pin 116 is progressively engaged with the bore 420 is not impeded.

To this end, a distance D41 may be defined between a nearer projection of the first and second projections 426, 428, ensuring that a user can grasp the control knob 424 and that the control knob 424 can rotate freely about a rotation axis 431. The distance D41 and the configuration of the control knob 424 may be chosen so that accidental release of the attachment, such as by the control knob 424 catching on outside objects like clothing, furniture, or otherwise, is minimized without compromising convenience and intuitiveness of use. A neck portion 436 of the control knob 424 may further distance the control knob 424 from a surface of the base 408, allowing for manipulation of the control knob 424 by a user.

The first and second projections 426, 428 may have any suitable configuration and material properties; in embodiments, the projections 426, 428 may be substantially rigid, such that the projections 426, 428 cannot be readily bent outward when a user grasps the control knob 424. In other embodiments, the projections 426, 428 may be at least partially flexible for ease and comfort of manipulating the control knob 424.

The lock mechanism 422, similar to previous embodiments, may define or comprise a pinion 456 that is arranged to engage with individual teeth 118 of the attachment pin 116, with a transverse bore 458 in which the lock mechanism 422 operates situated such that an appropriate degree of contact between the attachment pin 116 and the lock mechanism 422 is facilitated. The lock mechanism 422 may comprise a draft shaft 450 operatively connecting the pinion 456 to the control knob 424 along a length of the transverse bore 458. As in the previously described embodiment, a sleeve assembly 452 may be provided along the draft shaft 450.

The drive shaft 450 and the sleeve assembly 452 may cooperate with a one-way clutch device 460 to ensure that insertion of the attachment pin 116 is permitted to rotate the lock mechanism 422, while retaining the attachment pin 116 and accordingly the prosthetic liner 102 in place and preventing unwanted detachment of the prosthetic system components. The resilient element 466 may be arranged to bias the draft shift 450 into engagement with the attachment pin 116. Whereas the lock mechanism 122 of the embodiment shown in FIGS. 6 and 7 is configured such that depression of the control knob 124 urges the draft shaft 150 inwardly, thereby disengaging the pinion 156 from the notches 118 of the attachment pin 116, the lock mechanism 422 of the embodiment of FIGS. 10 and 11 is configured such that pulling on the control knob 424 urges the shaft 450 outwardly to disengage the pinion 456 from the notches 118 of the attachment pin 116.

As the control knob 424 is manipulated by a user, such as to pull the control knob 424 substantially outwardly away from the base 408, the resilient element 466 may be compressed and the pinion 456 may disengage from the attachment pin 116, allowing for quick release of the attachment pin, for example during doffing. When the user ceases from pulling on the control knob 424, the bias provided by the resilient element 466 returns the lock mechanism 422 to the engaged configuration. In this manner, the donning and doffing of the prosthetic system, and the attachment between components of the prosthetic system, may be deliberate, controlled, and intuitive, while avoiding catastrophic failure of the components.

The base 408 may define a main portion 472 through a portion of the thickness of which the bore 420 may be defined and through which the attachment pin 116 may extend. The main portion 472 may be flanked by connecting portions 474, elongate openings 476, wall segments 480, and other features as previously described. The main portion 472 may define a shape or profile 473 that is asymmetric and serves to, among other functions, reduce a bulk, weight, and cost of the socket 102. The depicted embodiment is merely exemplary, and the profile 473 may extend in any configuration, location, number, or extent. As described previously, the base 408 may also define an annular flange 484 proximate and/or surrounding the bore 420, the annular flange 484 sized and configured to guide the attachment pin 116 into the bore 420, further facilitating and easing the process of properly attaching the components of a prosthetic attachment system.

By providing a control knob operating with a lock mechanism corresponding to a prosthetic attachment system according to the embodiments of the disclosure, the problem of prosthetic systems being difficult or counter-intuitive to attach, particularly between a prosthetic liner and a prosthetic socket, is addressed. The arrangement and function of the control knob and lock mechanism of the disclosure advantageously provides an intuitive indicator of the attachment between an attachment pin and a pin bore, and further provides an intuitive and convenient manner of adjusting or releasing the degree of attachment between an attachment pin and a pin bore.

Although this disclosure describes certain exemplary embodiments and examples of a prosthetic socket system including a lock assembly, it nevertheless will be understood by those skilled in the art that the present disclosure extends beyond the specifically disclosed prosthetic socket and prosthetic attachment system embodiments to other alternative embodiments and/or users of the disclosure and obvious modifications and equivalents thereof. It is intended that the scope of the present disclosure should not be limited by the particular disclosed embodiments described above, and may be extended to prosthetic devices and supports, and other applications that may employ the features described herein.

The invention claimed is:

1. A lock assembly for connecting a distal end of a prosthetic liner to a distal end of a prosthetic socket, the lock assembly comprising:
    a base arranged to be supported by the distal end of the prosthetic socket, and defining a bore;
    an attachment pin arranged to be carried by the prosthetic liner and insertable through the bore;
    a lock mechanism arranged to be carried by the base and rotatable about a rotation axis, the lock mechanism including a control knob extending outwardly from a side of the base and having at least one elongate projection extending in a direction transverse relative to the rotation axis;
    wherein the attachment pin is arranged to interact with the lock mechanism as the attachment pin moves distally through the bore, and to cause the control knob to spin the at least one elongate projection about the rotation axis;
    wherein the at least one elongate projection extends obliquely a predetermined distance from and relative to a side of the base without interference from the base;
    wherein the at least one elongate projection extends radially from a central portion including the rotation axis;
    wherein an outer surface of the control knob includes at least one textured region configured to provide tactile feedback to a user.

2. The lock assembly of claim 1, wherein the lock mechanism is arranged so that the at least one projection of the control knob stops spinning about the rotation axis when the attachment pin is fully inserted in and/or through the bore to a predetermined extent.

3. The lock assembly of claim 1, wherein the lock mechanism comprises an engaging member operably communicating with the bore and adapted to selectively engage at least one notch among notches defined by the attachment pin as the attachment pin is inserted within and through the bore.

4. The lock assembly of claim 3, wherein the engaging member is a pinion connected to and extending along the rotatable axis of the control knob.

5. A lock assembly for connecting a distal end of a prosthetic liner to a distal end of a prosthetic socket, the lock assembly comprising:
    a base arranged to be supported by the distal end of the prosthetic socket, and defining a bore;
    an attachment pin arranged to be carried by the prosthetic liner and insertable through the bore, the attachment pin defining notches along a longitudinal length thereof;
    a lock mechanism arranged to be carried by the base and rotatable about a rotation axis, the lock mechanism including a control knob extending outwardly from a side of the base, the control knob having at least one elongate projection extending in a direction transverse relative to the rotation axis, the lock mechanism further comprising a pinion operably communicating with the bore and adapted to selectively engage at least one notch among the notches of the attachment pin as the attachment pin is inserted within and through the bore;
    wherein as the attachment pin is inserted through and within the bore, the control knob is arranged to spin the at least one elongate projection about the rotation axis;

wherein the at least one elongate projection extends obliquely a predetermined distance from and relative to a side of the base without interference from the base;

wherein the at least one elongate projection extends radially from a central portion including the rotation axis;

wherein an outer surface of the control knob includes at least one textured region configured to provide tactile feedback to a user.

6. The lock assembly of claim 5, wherein the lock mechanism comprises a shaft carrying the pinion at a first end and connecting a second end to the control knob, a sleeve assembly encompassing at least a portion of the shaft, a bearing and groove arrangement configured to provide cooperative movement between the sleeve assembly and the shaft, and a clutch device arranged to receive the sleeve assembly and to permit generally uniform rotation of the shaft, the sleeve assembly, the control knob, and the clutch device extending commonly along the rotatable axis.

7. The lock assembly of claim 6, wherein the shaft further includes a threaded portion located at the second end thereof, and a central portion interposed between the pinion and the threaded portion, the pinion is configured and arranged to engage the attachment pin such that teeth of the pinion mesh with notches of the attachment pin.

8. The lock assembly of claim 7, wherein the shaft defines at least one groove longitudinally extending along the central portion of the shaft, the at least one groove having a depth with contours to accommodate at least a portion of at least one ball bearing, the sleeve assembly defines along an interior surface thereof at least one groove located at or near a first end portion intended to be near or adjacent to the pinion, the sleeve assembly is positioned on the shaft such that the grooves of the sleeve assembly are aligned with the at least one groove of the shaft, a groove of the shaft and a corresponding groove of the sleeve assembly defining a pair of mutually opposed grooves, wherein the lock mechanism is configured such that the at least one ball bearing is seated in each pair of mutually opposed grooves of the shaft and the sleeve assembly, respectively.

9. The lock assembly of claim 8, wherein the at least one groove is arranged to permit the shaft to move within the sleeve assembly a predetermined distance until the pinion completely disengages from the notches of the attachment pin so as to permit the attachment pin to be freely removed from the lock assembly.

10. The lock assembly of claim 6, further comprising a coupler including a first end arranged to couple with the drive shaft, and a second end arranged to couple with the control knob, and a radially extending flange defined between the first and second ends.

11. The lock assembly of claim 10, further comprising a resilient member configured to engage between the radially extending flange and a seat flange of the clutch device, such that depression of the control knob urges travel of the drive shaft along a longitudinal axis of the lock mechanism, and rotation of the control knob rotates a direction about the rotation axis permitted by the clutch device.

12. The lock assembly of claim 11, wherein the resilient member is arranged to bias the drive shaft into a position whereat the pinion engages the notches of the attachment pin.

13. The lock assembly of claim 5, wherein the base comprises a body having a main portion and first and second connection portions extending outwardly and upwardly from a lower region of the main portion, the base forms open areas between the main portion and the first and second connection portions.

14. The lock assembly of claim 13, wherein the base further includes a pair of wall segments separated from one another by the main portion and extending between and connecting the first and second connecting portions.

15. The lock assembly of claim 5, wherein the base defines an annular flange surrounding the bore and extending axially upward from a top of the bore, the annular flange forming a conical inner surface configured to guide the attachment pin into the bore.

* * * * *